(12) United States Patent
Karavas et al.

(10) Patent No.: US 11,969,429 B2
(45) Date of Patent: *Apr. 30, 2024

(54) PEDIATRIC POWDER FOR ORAL SUSPENSION CONTAINING ANTIVIRAL AGENT AND METHOD FOR THE PREPARATION THEREOF

(71) Applicant: PHARMATHEN S.A., Pallini-Attikis (GR)

(72) Inventors: Evangelos Karavas, Pallini Attikis (GR); Efthymios Koutris, Pallini Attikis (GR); Vasiliki Samara, Pallini Attikis (GR); Ioanna Koutri, Pallini Attikis (GR); Anastasia Kalaskani, Pallini Attikis (GR); Lida Kalantzi, Pallini Attikis (GR); Andreas Kakouris, Pallini Attikis (GR); Amalia Diakidou, Pallini Attikis (GR); George Gotzamanis, Pallini Attikis (GR); Zaharias Georgousis, Pallini Attikis (GR); Manolis Fousteris, Pallini Attikis (GR)

(73) Assignee: PHARMATHEN S.A., Attikis (GR)

( * ) Notice: Subject to any disclaimer, the term of this patent is extended or adjusted under 35 U.S.C. 154(b) by 197 days.

This patent is subject to a terminal disclaimer.

(21) Appl. No.: 15/326,476

(22) PCT Filed: Jun. 19, 2015

(86) PCT No.: PCT/EP2015/001239
§ 371 (c)(1),
(2) Date: Jan. 14, 2017

(87) PCT Pub. No.: WO2016/008560
PCT Pub. Date: Jan. 21, 2016

(65) Prior Publication Data
US 2017/0202843 A1  Jul. 20, 2017

(30) Foreign Application Priority Data

Jul. 17, 2014  (WO) ............... PCT/EP2014/001951

(51) Int. Cl.
*A61K 31/522* (2006.01)
*A61K 9/00* (2006.01)
*A61K 9/14* (2006.01)
*A61K 9/16* (2006.01)

(52) U.S. Cl.
CPC .......... *A61K 31/522* (2013.01); *A61K 9/0053* (2013.01); *A61K 9/0095* (2013.01); *A61K 9/141* (2013.01); *A61K 9/145* (2013.01); *A61K 9/1629* (2013.01); *A61K 9/1652* (2013.01)

(58) Field of Classification Search
None
See application file for complete search history.

(56) References Cited

U.S. PATENT DOCUMENTS

| | | | |
|---|---|---|---|
| 2005/0036977 A1* | 2/2005 | Gole | A61K 47/585 424/76.1 |
| 2007/0215511 A1 | 9/2007 | Mehta et al. | |
| 2009/0202635 A1* | 8/2009 | Scott | A61K 9/0056 424/468 |
| 2012/0149720 A1* | 6/2012 | Goswami | A61P 31/22 514/263.37 |
| 2013/0177520 A1* | 7/2013 | Kakumanu | A61K 31/495 424/78.1 |

FOREIGN PATENT DOCUMENTS

| | | | | |
|---|---|---|---|---|
| WO | WO-2009049648 A2 * | 4/2009 | ........... | A61K 9/2009 |
| WO | 2010143207 A1 | 12/2010 | | |

OTHER PUBLICATIONS

Kim, J.-I., et al., International Journal of Pharmaceutics 455: 31-39. (Year: 2013).*
Helmy, A., et al., International Journal of Drug Delivery, 4: 198-208. (Year: 2012).*
Sharma, V. and C. Chauhan, Journal of Drug Delivery and Therapeutics 4(4): 115-123 (2014). (Year: 2014).*
Dahima, R. and R. Sharma, Asian Journal of Pharmaceutics 2010: 110-115. (Year: 2010).*
Database WPI Week 200410, Thomson Scientific, London, GB, AN 2004-094168, XP002743585, & JP 2004002245 A, Jan. 8, 2004, Abstract.
Written Opinion of the ISR, WIPO,PCT/EP2015/001239.

* cited by examiner

Primary Examiner — David J Blanchard
Assistant Examiner — Daniel F Coughlin
(74) Attorney, Agent, or Firm — AKC PATENTS, LLC; Aliki K. Collins

(57) ABSTRACT

The present invention relates to a pediatric powder for reconstitution as suspension for oral administration comprising a therapeutically effective amount of an antiviral agent or pharmaceutical acceptable salt or derivative thereof, in particular Valaciclovir in complex with an ion exchange resin in a specific ratio in order to obtain a palatable and child-friendly product. It also relates to a process for the preparation thereof.

9 Claims, No Drawings

PEDIATRIC POWDER FOR ORAL SUSPENSION CONTAINING ANTIVIRAL AGENT AND METHOD FOR THE PREPARATION THEREOF

TECHNICAL FIELD OF THE INVENTION

The present invention relates to a stable pharmaceutical formulation for oral administration containing a therapeutically effective quantity of an antiviral agent, and more particularly Valaciclovir or pharmaceutical acceptable salt or derivative thereof, and a method for the preparation thereof.

BACKGROUND OF THE INVENTION

Acyclovir is a known compound widely used for the treatment of viral infections, particularly infections caused by the herpes virus. Pharmacokinetic studies have shown that acyclovir is poorly water soluble and presents poor oral bioavailability, therefore intravenous administration is required in order to achieve high concentrations in the plasma.

Valaciclovir or L-valyl acyclovir is a prodrug of acyclovir, and has been shown to possess antiviral properties. It is used for the treatment of the same types of infections as acyclovir. More specifically, it is used for varicella zoster virus infections-herpes zoster, herpes simplex virus infections and cytomegalovirus infections.

A preferred form of Valaciclovir is the Valaciclovir hydrochloride salt. After oral administration, Valaciclovir hydrochloride is rapidly absorbed from the gastrointestinal tract and nearly completely converted to acyclovir and L-valine by first-pass intestinal and/or hepatic metabolism by enzymatic hydrolysis. It has been shown that Valaciclovir provides a high bioavailability of acyclovir, much higher than that obtained with oral acyclovir, and is equivalent to plasma levels achieved with doses of intravenous acyclovir.

The chemical name of Valaciclovir hydrochloride is L-valine, 2-[(2-amino-1, 6-dihydro-6-oxo-9H-purin-9-yl) methoxy] ethyl ester, mono hydrochloride and its molecular formula is $C_{13}H_{20}N_6O_4 \cdot HCl$ corresponding to a molecular weight of 360.80 (for HCl salt) and 324.34 (for free base). It is a white to off-white crystalline powder. Valaciclovir hydrochloride is soluble in water and insoluble in dichloromethane, the maximum solubility in water at 25° C. is 174 mg/mL.

EP 1023899 A1 discloses an aqueous pharmaceutical preparation comprising an antiviral agent having a purine skeleton or a pyrimidine skeleton or a pharmaceutically acceptable salt thereof; an agent for inhibiting crystal-separation such as acetyl tryptophan and water.

WO 2011/075691 A1 discloses a method of administering an antiviral agent to a patient, the method comprising the steps of: (a) providing a powdered composition comprising an antiviral agent and a protein or a hydrolyzed protein; (b) mixing the powdered composition with a liquid or semi-solid to form a stable solution or dispersion in which the protein or the hydrolyzed protein is bound to the pharmaceutically active compound; and (c) orally administering the solution or dispersion to the patient.

Although each of the patents above represents an attempt to provide a stable and patient-friendly Valaciclovir composition for oral administration, there still remains the need in the art for age-adapted dosage forms appropriate for children. In particular, there is a need for safe and effective taste masked liquid formulations ideal for children.

SUMMARY OF THE INVENTION

It is, therefore, an object of the present invention to provide a liquid formulation for oral administration containing an antiviral agent, and in particular Valaciclovir or pharmaceutical acceptable salt or derivative thereof as an active ingredient, which is adequate for pediatric use.

The main object of the present invention is to provide a powder for reconstitution as suspension for oral administration comprising Valaciclovir, which achieves to mask the bitter taste of the active ingredient and provides acceptable palatability.

Another object of the present invention is the selection of the optimal combination of pharmaceutical acceptable excipients and method of preparation in order to achieve the appropriate dissolution profile and stability for the finished dosage form.

Moreover, it is another object of the present invention to provide a powder for oral suspension comprising Valaciclovir, which can be formulated into dosage forms of different strengths by proportionally adjusting the amounts of the pharmaceutically acceptable excipients, as well as the active compound Valaciclovir.

A further approach of the present invention is to provide a powder for oral suspension comprising Valaciclovir or pharmaceutical acceptable salt or derivative thereof which is manufactured through a fast, simple and cost-effective process.

In accordance with the above objects of the present invention, a pharmaceutical composition for oral administration is provided comprising Valaciclovir in complex with a resin, wherein the ratio of Valaciclovir to the resin is 1:0.8.

According to another embodiment of the present invention, a process for the preparation of a powder for reconstitution as suspension, comprising an antiviral agent such as Valaciclovir or pharmaceutical acceptable salt or derivative thereof as an active ingredient in complex with a resin wherein the ratio of Valaciclovir to the resin is 1:0.8 is provided, which comprises the following steps:
 Dry blending of drug:resin in the ratio 1:0.8;
 Kneading the above blend with water;
 Drying of the wet mass at 40° C.;
 Milling of the drug-resin complex until particle size gets less than 250 µm;
 Dry mixing of the drug-resin complex and the excipients of the internal phase;
 Mixing with the excipients of the external phase;
 Shifting the powder to eliminate any clumps.

Furthermore, a suspension for oral administration is provided by mixing a powder with a suitable aqueous diluent.

Other objects and advantages of the present invention will become apparent to those skilled in the art in view of the following detailed description.

DETAILED DESCRIPTION OF THE INVENTION

For the purposes of the present invention, a pharmaceutical composition comprising an active ingredient is considered to be "stable" if said ingredient degrades less or more slowly than it does on its own and/or in known pharmaceutical compositions.

As already mentioned the main object of the present invention is to provide a stable pharmaceutical composition of Valaciclovir or pharmaceutical acceptable salt or derivative thereof for oral administration appropriate for children.

Because of physiological and pharmacokinetic differences between the adult and pediatric population there is the need for the development of formulations specifically studied and designed for children. In children gastric emptying time and gastric pH is variable, and there are differences in the surface area of the absorptive sites and gastrointestinal permeability. There are also reported changes in the biliary function depending upon age, body water and adipose tissue, which may lead to differences in drug disposition and elimination. In most cases, a child's dose is calculated based on the body weight, whereas a few cases based on body surface are also in use.

An ideal formulation for children will allow minimal dosage and frequency; will have minimal impact on lifestyle; a minimum of nontoxic excipients and will have convenient, easy and reliable administration.

Children are a very heterogeneous population that includes newborns, infants, toddlers, pre-schoolers, school-age children and adolescents. Therefore, there is the need to develop formulations appropriate for all the pediatric sub-populations that will use the products. Liquid formulations (solutions, suspensions, syrups, etc) have been popular because of the ease of administering them to children of different ages and the ease of dosing more precisely according to body weight or body surface area. Liquid medicines for oral administration are usually recommended for infants and younger children so the ability to mask unpleasant taste is crucial.

The present invention proposes a palatable powder that is reconstituted in a suspension for children from birth through 18 years of age. Therefore, the proposed invention covers children of all ages and all children can be dosed on the same manner, i.e. on a 'per Kg' basis. Without being limited volumes to be administered for varicella indication (dose: 20 mg/kg) and herpes labialis indication (dose: 30 mg/kg) depend on strength and child's weight.

The main advantage of the powder to be reconstituted in a suspension instead of a ready-made liquid formulation of Valaciclovir is the favourable stability of the product throughout its self-life, as stability problems have been reported when Valacyclovir is formulated as a ready-made liquid.

The most important problem encountered at the development of Valaciclovir formulations of the present invention was the extremely bitter taste of active ingredient. Taste is an important parameter in administering drugs orally. In paediatric patients, acceptance of a dosage form is primarily dependent on a child's taste preference. Different taste masking technologies have been used to address the problem of patient compliance. Taste masking of water soluble bitter drugs, especially those with a high dose, is difficult to achieve by using sweeteners alone. As a consequence, more efficient techniques such as coating, microencapsulation and granulation have been used in combination with the sweeteners.

The powder for oral suspension proposed by the present invention comprises a complex of Valaciclovir with an ion exchange resin in a specific ratio in order to obtain a palatable and child-friendly product.

The powder for oral suspension of the present invention may also contain suspending agents and pH agents.

Suspending agents form films around particles and decrease interparticle attraction. Suspending agents also act as thickening agents. They increase the viscosity of the solution, which is necessary to prevent sedimentation of the suspended particles as per Stokes' law. Property of a well formulated suspension is that it can be easily re-suspended by the use of moderate agitation.

Suspending agents may be selected from alginates, acacia, carboxymethylcellulose, hydroxypropylcellulose, hydroxypropylmethylcellulose, xanthan gum, tragacanth. The preferred compositions of the present invention comprise preferably xanthan gum.

pH agents are additives used to control pH. They may be selected from hydrochloric acid, sodium hydroxide, sodium hydrogen sulphate, tri-sodium citrate dihydrate. The preferred compositions of the present invention comprise preferably sodium hydroxide or tri-sodium citrate dihydrate.

Ion exchange Resins (IER) were extensively used in the development of formulations of the present invention as taste masking agents. IERs are solid and suitably insoluble high molecular weight polyelectrolytes that can exchange their mobile ions of equal charge with the surrounding medium. The resulting ion exchange is reversible and stoichiometric with the displacement of one ionic species by another. Research over the last few years has revealed that IERs are equally suitable for drug delivery technologies, including controlled release, transdermal, nasal, topical and taste masking. Being high molecular weight water insoluble polymers, the resins are not absorbed by the body and are therefore inert.

Since most drugs possess ionic sites in their molecule, the resin's charge provides a means to loosely bind such drugs and this complex prevents the drug release in the saliva, thus resulting in taste masking. The nature of the drug resin complex formed is such that the average pH of 6.7 and cation concentration of about 40 meq/L in the saliva are not able to break the drug resin complex but it is weak enough to be broken down by hydrochloric acid present in the stomach. Thus, the drug resin complex is absolutely tasteless with no after taste, and at the same time, its bioavailability is not affected.

A critical factor to prepare a Drug-Resin complex (DRC) was the choice of the right IER. Valaciclovir·HCl contains an exchangeable secondary amine moiety i.e. cationic center. Therefore, cation exchange resins are highly recommended for the complex formation. Weak cation acid ion exchange resins such as INDION™ 204, INDION™ 214 as well as a strong cation acid resin such as PUROLITE™ C100CaMR were tested in order to form the DRC.

Mediums of different pH were examined in order to achieve the maximum drug loading into the resin. For this reason, the pH of solutions was adjusted at 3, 4, 5, 6, and 7. The drug loaded was evaluated spectrophotometrically. The % w/w unbound drug for pH 3, 4, 5, 6, 7 and water was found to be 79.85%±2.19%, 75.24%±2.91%, 66.69%±2.76%, 61.19%±2.61%, 30.91%±2.53% and 72.61%±2.81% respectively. Buffer pH=7 enhanced more the effect of drug loading.

The next step was to examine the effect of drug loading into the resin for buffer pH=7 of different ion strength. For this reason, buffer pH=7 of normality 0.1N, 0.2N, 1N were prepared and the drug loaded was evaluated spectrophotometrically as before. Buffer pH=7 0.2N was the most suitable medium as the higher drug loading was reached. (61.60%±2.05%).

At this point of studies, the research focused on the type of IER. For this reason, resins of different functional group were examined to reach the higher drug loading. The % w/w unbound drug for INDION™ 204, INDION™ 214, KYRON™ T-134, KYRON™ T-314, PUROLITE™ C115KMR and PUROLITE™ C100CaMR was found to be 30.91%.+−.1.97%, 44%.+−.2.95%, 59.95%.+−.2.96%, 87.99%.+−.1.67%, 58.42%.+−.2.93% and 21.80%.+−.1.29% respectively. As a result, PUROLITE™ C100CaMR and INDION™ 204 were the most preferred resins that could form hydrogen bonds with the cationic center of Valaciclovir and prevent the release in saliva.

Another important factor that was examined was the quantity of water used for the preparation of the drug-resin complex. The wet granulation method was selected for the DRC preparation as it could perform a stable, easy-to use complex with a neutral taste. It was observed that excessive amounts of water led to a DRC that didn't release the drug even in the stomach environment. DRCs of different Drug:Resin:Water ratio were tested in order to determine the appropriate water quantity. Optimum dissolution profile was achieved when Drug:Resin in the ratio 1:0.8 was granulated with water according to ratio Drug:Resin:Water 1:0.8:0.5.

It is possible to prepare dosage forms of different strength using appropriate quantity of the same composition, thereby limiting the cost of production and minimizing the number, and consequently the cost of clinical studies required for the approval of the product by the authorities.

The following examples illustrate preferred embodiments in accordance with the present invention without limiting the scope or spirit of the invention:

EXAMPLES

Both INDION™ 204 and PUROLITE™ C100CaMR were evaluated for their taste/feel acceptability and drug contamination status. Formulations 1 to 3 of Drug:Resin 1:1, 1:0.8, 1:0.5 respectively were prepared for both resins and the palatability was estimated by a three person panel. For each Formulation 1 to 3 a composition without resin was also examined in order to assess the impact of resins as taste masking agents. (Table 1). The process chosen for the preparation of Formulations 1 to 3 was wet and dry mixing following the below steps:

Dry blending of Drug:Resin;
Kneading the above blend with water;
Drying of the wet mass at 40° C.;
Milling of DRC until particle size gets less than 250 μm;
Dry mixing of the DRC and the excipients of the internal phase;
Mixing with the excipients of the external phase;
Shifting the powder to eliminate any clumps;
Reconstitution of powder with suitable aqueous diluent.

TABLE 1

Formulations 1 to 3

| Ingredients | Drug:Resin | | | | | |
|---|---|---|---|---|---|---|
| | 1:1 Formulation 1 | | 1:0.8 Formulation 2 mg/ml | | 1:0.5 Formulation 3 | |
| Internal phase | | | | | | |
| Valaciclovir | 50.000 | 50.000 | 50.000 | 50.000 | 50.000 | 50.000 |
| Valaciclovir HCl hydrated | 56.180 | 56.180 | 56.180 | 56.180 | 56.180 | 56.180 |
| IER | 50.000 | — | 40.000 | — | 25.000 | — |
| Xanthan gum | 4.167 | 4.167 | 4.167 | 4.167 | 2.083 | 2.083 |
| Microcrystalline cellulose | 8.333 | 8.333 | 8.333 | 8.333 | 8.333 | 8.333 |

TABLE 1-continued

Formulations 1 to 3

| Ingredients | Drug:Resin | | | | | |
|---|---|---|---|---|---|---|
| | 1:1 Formulation 1 | | 1:0.8 Formulation 2 mg/ml | | 1:0.5 Formulation 3 | |
| Sucralose | 1.667 | 1.667 | 1.667 | 1.667 | 1.667 | 1.667 |
| Methyl paraben | 0.083 | 0.083 | 0.083 | 0.083 | 0.083 | 0.083 |
| NaOH | 8.333 | 8.333 | 8.333 | 8.333 | 8.333 | 8.333 |
| External phase | | | | | | |
| Orange flavour | 0.167 | 0.167 | 0.167 | 0.167 | 0.167 | 0.167 |
| Talc | 8.333 | 8.333 | 8.333 | 8.333 | 8.333 | 8.333 |
| Total solids | 137.263 | 87.263 | 127.263 | 87.263 | 110.179 | 85.179 |

The characteristics of the suspension produced for both resins are presented in Table 2 below:

TABLE 2

Characteristics of Formulations 1 to 3 for INDION™ 204, PUROLITE™ C100Ca and without resin

| | INDION™ 204 | | PUROLITE™ C100Ca | | Without resin | |
|---|---|---|---|---|---|---|
| | pH | Appearance | pH | Appearance | pH | Appearance |
| Formulation 1 | 5.55 | Homogenous suspension | 5.63 | Homogenous suspension | 5.78 | Two phase suspension |
| Formulation 2 | 5.51 | Homogenous/ compact | 5.54 | Homogenous/ compact | 5.84 | Two phase suspension |
| Formulation 3 | 5.70 | Homogenous suspension | 5.81 | Homogenous suspension | 5.98 | Two phase suspension |

In Formulation 1 both compositions of resins were homogeneous and they had a smooth feeling on the tongue. It seems that in composition with Purolite C100Ca, the taste wasn't desirable enough because it had a more acidic taste due to its strong nature. Despite this fact, it is obvious that both resins can taste mask the extremely bitter taste of drug as the composition without resin didn't have a desirable taste. Also, the formula without resin wasn't indicated as a two phase suspension was noticed after the reconstitution.

In Formulation 2 both compositions of resins had a desirable aftertaste in contrast to that one without resin where the bitter taste of drug confirmed the efficacy of resins. In this case, the strong acid character of Purolite C100Ca didn't affect the taste of the composition due to its lower concentration (40 mg/ml instead of 50 mg/ml). As for their appearance, probably the concentration of suspending agent-Xanthan gum (4.167 mg/ml) was high enough and as a result, the compositions had a poor flow.

In Formulation 3 both compositions of resins had enhanced palatability compared to that one without resin but it is evident that the resin concentration (25 mg/ml) wasn't adequate to taste mask the API.

Taking Formulations 1 to 3 into consideration, a composition with a totally accepted palatability isn't yet reached but there are serious indications that DRC 1:0.8 is probably a desirable complex.

Apart from the palatability screening, a focus on the drug's degradation effect would enhance the research around the most suitable Drug:Resin ratio and appropriate resin. For this reason, the impurities status of DRC 1:1, 1:0.8, 1:0.5 for both resins was recorded with an HPLC method. Impurities data at the zero point are presented in the following tables (Table 3 and 4).

TABLE 3

Impurities data of DRC 1:1, 1:0.8, 1:0.5 for INDION™ 204

| Specification | DRC 1:0.5 | DRC 1:0.8 | DRC 1:1 |
|---|---|---|---|
| Guanine (NMT 0.5%) | 0.03 | 0.03 | 0.04 |
| Acyclovir (NMT 3.0%) | 0.73 | 0.69 | 0.68 |
| Formyl VACV (NMT 0.5%) | 0.13 | 0.13 | 0.14 |
| BVG (NMT 0.5%) | ND | ND | ND |
| Unknown | ND | ND | ND |
| Unknown | ND | ND | ND |
| Unknown | ND | ND | ND |
| Unknown | ND | ND | ND |
| Unknown | ND | ND | ND |
| Total | 0.89 | 0.85 | 0.85 |

TABLE 4

Impurities data of DRC 1:1, 1:0.8, 1:0.5 for PUROLITE™ C100Ca

| Specification | DRC 1:0.5 | DRC 1:0.8 | DRC 1:1 |
|---|---|---|---|
| Guanine (NMT 0.5%) | 0.07 | 0.22 | 0.36 |
| Acyclovir (NMT 3.0%) | 0.67 | 0.71 | 0.78 |
| Formyl VACV (NMT 0.5%) | 0.14 | 0.16 | 0.17 |
| BVG (NMT 0.5%) | ND | ND | ND |
| Unknown | ND | ND | ND |
| Unknown | ND | ND | ND |
| Unknown | ND | ND | ND |
| Unknown | ND | ND | ND |
| Unknown | ND | ND | ND |
| Total | 0.88 | 1.09 | 1.31 |

It is evident that PUROLITE™ C100Ca degrades to a greater extent the drug than the INDION™ 204. More specifically, increasing the Drug: PUROLITE™ C100 ratio both guanine and acyclovir, the major metabolite of drug, follow an increasing trend. This behavior doesn't appear to Drug:INDION™ 204 complex of any ratio.

As a result, INDION™ 204 appears as the most suitable resin for the Valaciclovir development and the DRC 1:0.8 and 1:1 are highly recommended due to their lower drug degradation effect. Bearing in mind the palatability screening of Formulations 1, 2 and 3 it is concluded that Drug: INDION™ 204 1:0.8 complex is the most appropriate for the development of Valaciclovir.

Consequently, in Formulation 4 Drug:INDION™ 204 with ratio 1:0.8 was used. Moreover, xanthan gum was reduced to 50% w/w of initial quantity as its high concentration results in poor flow. A homogeneous suspension of an acceptable taste was prepared. (Table 5)

Despite this, there is an emergency to reduce the total solids per ml as the preparation of the 100 mg/ml strength, which would follow the weight proportional rule, would encounter a few problems. In Formulation 5 microcrystalline cellulose was erased from the formula as it was slightly detectable on the tongue and even though orange flavor concentration was decreased, the increase in sucralose concentration was sufficient in order to offer desirable taste. (Table 5) Formulation 5 was difficult to be reconstituted; the extremely high quantity of NaOH impedes the powder reconstitution. It is common knowledge that NaOH is a quite strong base and leads to an exothermic reaction posing a threat to development safety.

TABLE 5

Formulations 4 and 5

| | mg/ml | |
|---|---|---|
| Ingredients | Formulation 4 | Formulation 5 |
| Internal Phase | | |
| Valaciclovir | 50.000 | 50.000 |
| Valaciclovir HCL hydrated | 56.180 | 56.180 |
| INDION™ 204 | 40.000 | 40.000 |
| Xanthan Gum | 2.083 | 2.500 |
| Microcrystalline Cellulose | 8.333 | — |
| Sucralose | 1.667 | 2.500 |
| Methyl Paraben | 0.083 | 0.083 |
| NaOH | 8.333 | 8.333 |
| External Phase | | |
| Orange flavour | 0.167 | 0.083 |
| Talc | 8.333 | 1.667 |
| Total solids | 125.179 | 111.346 |

Formulations 4 and 5 were prepared with the same manufacturing process as Formulations 1 to 3.

In order to examine how the ratio Xanthan gum:NaOH influence the pH and appearance of compositions, Formulations 6 and 7 with different ratios were prepared. (Table 6) The manufacturing process followed was the same as in Formulations 1 to 3.

TABLE 6

Formulations 6 and 7

| | mg/ml | |
|---|---|---|
| Ingredients | Formulation 6 | Formulation 7 |
| Internal Phase | | |
| Valaciclovir | 50.000 | 50.000 |
| Valaciclovir Hydrochloride hydrated | 56.180 | 56.180 |
| INDION™ 204 | 40.000 | 40.000 |
| Xanthan Gum | 3.333 | 2.292 |
| Sucralose | 2.500 | 2.500 |
| Methyl Paraben | 0.083 | 0.083 |
| NaOH | 5.000 | 6.167 |
| External Phase | | |
| Orange flavour | 0.083 | 0.083 |
| Talc | 1.667 | 1.667 |
| Total solids | 108.846 | 108.972 |

Formulation 7 with 6.167 mg/ml NaOH and 2.292 mg/ml xanthan gum was suitable to prepare a homogeneous suspension with a highly acceptable taste. There is no need to adjust the pH of the composition as NaOH forms Van der Waals bonds with the free ions of API hydrochloride (Cl—) that coexist after the Drug:Resin complexation. INDION™ 204 is used to taste mask the bitter taste of drug. However, many references in the literature confirm a wide range of applications as controlled release vehicle as well. This behavior would change dramatically the pharmacokinetics of the development and that's why a dissolution method was immediately applied. The dissolution rate of the drug was recorded using USP II apparatus (paddles) at 50 rpm and 900 ml HCl 0.1N. (Table 7)

TABLE 7

Dissolution results of DRC 1:0.8 and Formulation 7

| Time (min) | DRC 1:0.8 | Formulation 7 | Target |
|---|---|---|---|
| 10 | 95.88% | 97.02% | >85% |
| 15 | 97.04% | 98.00% | |
| 20 | 97.83% | 98.47% | |
| 30 | 98.87% | 98.03% | |
| 45 | 99.83% | 98.61% | |

It is concluded that INDION™ 204 didn't sustain the drug release in the dissolution medium, but on the contrary, the drug content was delivered immediately. Both the complex and the formulation release more than 85% drug at 15 min. Consequently, Formulation 7 fulfilled the expectations for the powder for oral suspension of 50 mg/ml strength. The composition of the 100 mg/ml strength follows the weight proportionality rule.

Alternative formulations were prepared in order to examine the role of the pH agent and the suspending agent into the product development. Two different excipients were replaced: NaOH (pH agent) and Xanthan gum (suspending agent).

Firstly, NaOH was replaced by tri-sodium citrate dihydrate. (Table 8) As a conjugate base of a weak acid, citrate can perform as a buffering agent or acidity regulator, resisting changes in pH.

TABLE 8

Formulations 8 and 9

| | mg/ml | |
|---|---|---|
| Ingredients | Formulation 8 | Formulation 9 |
| Internal Phase | | |
| Valaciclovir | 50.000 | 50.000 |
| Valaciclovir Hydrochloride hydrated | 56.180 | 56.180 |
| INDION ™ 204 | 40.000 | 40.000 |
| Xanthan Gum | 3.333 | 2.292 |
| Sucralose | 2.500 | 2.500 |
| Methyl Paraben | 0.083 | 0.083 |
| Tri-sodium citrate dihydrate | 22.792 | 33.208 |
| External Phase | | |
| Orange flavour | 0.083 | — |
| Talc | 1.667 | 1.667 |
| Total solids | 126.638 | 135.930 |

Formulations 8 and 9 were prepared with the same manufacturing process as Formulations 1 to 3.

Both formulations led to a homogeneous suspension of good flow. Formulation 8 had a slightly acidic taste that derives probably from the orange flavor and the pH was at a low level. So, Formulation 9 was prepared with increased concentration of pH agent and the orange flavor was erased. The taste was importantly enhanced and the pH was increased.

Formulation 8 is similar to the formulation prepared with NaOH (Formulation 6) apart from pH agent concentration. This is predictable due to their nature. NaOH is an extremely strong base in contrast to tri-Sodium citrate that is a weak base.

The % w/w drug release and the dissolution profile of Formulation 9 in HCL 0.1N is shown in the table below.

TABLE 9

Dissolution results of DRC 1:0.8 and Formulation 9

| Time (min) | DRC 1:0.8 | Formulation 9 | Target |
|---|---|---|---|
| 10 | 95.88% | 98.54% | >85% |
| 15 | 97.04% | 99.16% | |
| 20 | 97.83% | 99.00% | |
| 30 | 98.87% | 99.64% | |
| 45 | 99.83% | 100.94% | |

It is evident from tables 7 and 9 that both pH agents (NaOH and Tri-sodium citrate dihydrate) didn't sustain the drug release as the intermolecular bonds between drug and resin break immediately in HCL 0.1N.

The taste of Formulation 9 was absolutely acceptable and the homogeneous appearance fulfilled all expectations. The composition of the 100 mg/ml strength follows the weight proportionality rule.

Xanthan gum was replaced with hydroxypropyl cellulose and hydroxypropylmethyl cellulose.

The characteristics of the formulations comprising HPC and HPMC instead of xanthan gum were not estimated as none of suspending agents used prepared a homogeneous suspension. It seems that the cellulose derivatives were not compatible with the other excipients. As a result, it is concluded that xanthan gum appears as a suitable suspending agent having also good stability and viscosity properties over a wide pH and temperature range.

The preferred compositions of the present invention are illustrated in table 10 below.

TABLE 10

Preferred compositions of the present invention

| Ingredients | mg/ml | |
|---|---|---|
| Internal Phase | | |
| Valaciclovir | 50.000 | 50.000 |
| Valaciclovir Hydrochloride hydrated | 56.180 | 56.180 |
| INDION ™ 204 | 40.000 | 40.000 |
| Xanthan Gum | 2.292 | 2.292 |
| Sucralose | 2.500 | 2.500 |
| Methyl Paraben | 0.083 | 0.083 |
| NaOH | 6.167 | — |
| Tri-sodium citrate dihydrate | — | 33.208 |
| External Phase | | |
| Orange flavour | 0.083 | — |
| Talc | 1.667 | 1.667 |
| Total solids | 108.972 | 135.930 |

The compositions of 100 mg/ml strength follow the weight proportionality rule.

The preferred compositions of the present invention are prepared according to the following manufacturing process:

Dry blending of Drug:INDION™ 204 in the ratio 1:0.8;

Kneading the above blend with water in the ratio Drug:INDION™ 204:Water 1:0.8:0.5;

Drying of the wet mass at 40° C.;

Milling of the Drug-INDION™ 204 complex until particle size gets less than 250 μm;

Dry mixing of the Drug-INDION™ 204 complex and the excipients of the internal phase;

Mixing with the excipients of the external phase;

Shifting the powder to eliminate any clumps;

Reconstituting the powder with suitable aqueous diluent.

While the present invention has been described with respect to the particular embodiments, it will be apparent to those skilled in the art that various changes and modifications may be made in the invention without departing from the spirit and scope thereof, as defined in the appended claims.

The invention claimed is:

1. A powder comprising Valaciclovir or pharmaceutical acceptable salt or derivative thereof and an ion exchange resin, wherein Valaciclovir is in complex with the ion exchange resin forming Drug-Resin complex (DRC) particles, wherein each DRC particle comprises hydrogen bonds between the ion exchange resin and a cationic center of Valaciclovir, and wherein the ratio of Valaciclovir to the ion exchange resin in the DRC particle is 1:0.8, and wherein the powder further comprises a suspending agent and a pH agent, and wherein the suspending agent forms a film around each DRC particle and the film decreases interparticle attraction, and wherein the powder is configured to be reconstituted with an aqueous diluent as suspension for oral administration, and wherein the powder comprises a dissolution profile where more than 95% of Valaciclovir is released from complexation with the ion exchange resin at 10 minutes when suspended in 900 ml HCl 0.1N.

2. The powder according to claim 1, wherein the ion exchange resin is a cationic acid ion exchange resin.

3. The powder according to claim 1, wherein the suspending agent is xanthan gum and the pH agent is selected from sodium hydroxide or tri-sodium citrate dihydrate.

4. The powder according to claim 1, wherein it is appropriate for children from birth through 18 years of age.

5. A process for preparing a suspension comprising mixing a powder as claimed in claim 1 with a suitable aqueous diluent.

6. The powder according to claim 1, wherein the ion exchange resin comprises a weak cation acid ion exchange resin or a strong cation acid ion exchange resin.

7. The powder according to claim 1, wherein the DRC particles have a size less than 250 μm.

8. The powder according to claim 1, wherein the ratio of the suspending agent to the pH agent is in the range of 0.069 to 0.37.

9. A powder for oral suspension comprising Valaciclovir or a pharmaceutical acceptable salt thereof in complex with an ion exchange resin, a suspending agent and a pH adjusting agent, wherein the ratio of Valaciclovir to the ion exchange resin is 1:0.8, and wherein Valaciclovir is the only active pharmaceutical ingredient.

* * * * *